(12) United States Patent
Feng et al.

(10) Patent No.: US 8,887,724 B2
(45) Date of Patent: Nov. 18, 2014

(54) OXYGEN SENSOR SEAT ASSEMBLY, OXYGEN SENSOR ASSEMBLY, AND ANESTHESIA MACHINE

(75) Inventors: Wanchun Feng, Shenzhen (CN); Peitao Chen, Shenzhen (CN); Geoffrey C. Jawidzik, Mahwah, NJ (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 445 days.

(21) Appl. No.: 13/252,064

(22) Filed: Oct. 3, 2011

(65) Prior Publication Data

US 2012/0085435 A1    Apr. 12, 2012

(30) Foreign Application Priority Data

Oct. 9, 2010    (CN) .......................... 2010 1 0501417

(51) Int. Cl.
| | | |
|---|---|---|
| A61M 15/00 | (2006.01) | |
| A61M 16/00 | (2006.01) | |
| A61M 16/10 | (2006.01) | |
| F16K 31/02 | (2006.01) | |
| A62B 7/00 | (2006.01) | |
| A62B 9/02 | (2006.01) | |
| A61M 16/01 | (2006.01) | |
| A61M 16/20 | (2006.01) | |

(52) U.S. Cl.
CPC .............. *A61M 16/01* (2013.01); *A61M 16/20* (2013.01); *A61M 2016/1025* (2013.01); *A61M 2205/70* (2013.01)
USPC ............ 128/205.24; 128/204.23; 128/203.12; 128/203.14

(58) Field of Classification Search
CPC .............. A61M 16/20; A61M 16/208; A61M 2230/00; A61M 2230/40; A61M 2230/435; G01D 11/30
USPC ............ 128/205.24, 203.12, 202.22, 202.27; 73/866.5

See application file for complete search history.

(56) References Cited

U.S. PATENT DOCUMENTS

| | | | |
|---|---|---|---|
| 4,061,160 A | 12/1977 | Kashmer et al. | |
| 4,489,590 A | 12/1984 | Hadden | |
| 4,590,789 A | 5/1986 | Kunze | |
| 2007/0051367 A1 * | 3/2007 | Mashak et al. | 128/203.12 |
| 2009/0272205 A1 * | 11/2009 | Brown et al. | 73/866.5 |

FOREIGN PATENT DOCUMENTS

| | | |
|---|---|---|
| EP | 0319933 A2 | 6/1989 |
| FR | 2692352 A3 * | 12/1993 |

OTHER PUBLICATIONS

Zhu, Xing, "Design an oxygen supply device synchronized with breath," The General Hospital of Nanjing Military Area, Nanjing Jiangsu 210002, China, Sep. 2002, pp. 4-6.

Feng, Li-jian, "Working Principle and Performance Testing of Oxygen Battery in Ventilator," China Academic Journal Electronic Publishing House, Nov. 4, 2008, pp. 57-58.

* cited by examiner

*Primary Examiner* — Kristen Matter
(74) *Attorney, Agent, or Firm* — Kory D. Christensen; Stoel Rives LLP

(57) ABSTRACT

An oxygen sensor seat assembly, an oxygen sensor assembly, and an anesthesia machine are disclosed.

23 Claims, 10 Drawing Sheets

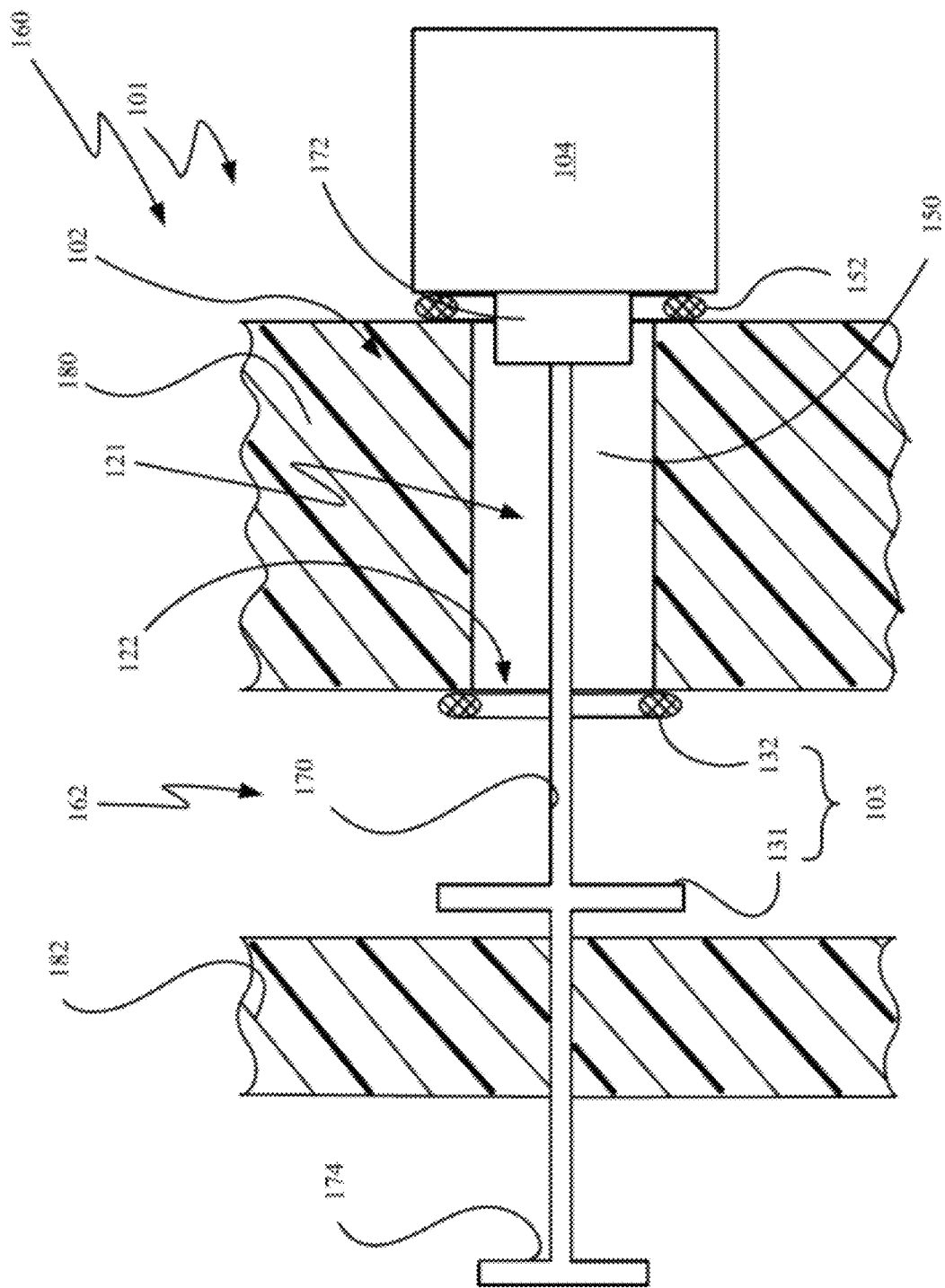

OXYGEN SENSOR SEAT ASSEMBLY, OXYGEN SENSOR ASSEMBLY, AND ANESTHESIA MACHINE

CROSS-REFERENCE TO RELATED APPLICATIONS

This application claims the benefit of Chinese Patent Application No. 201010501417.8, filed Oct. 9, 2011, which is incorporated herein by reference in its entirety.

TECHNICAL FIELD

The following disclosure relates to the field of anesthesia machines.

SUMMARY OF THE INVENTION

Disclosed herein are embodiments of an oxygen sensor assembly applied to a breathing system gas path of an anesthesia machine

BRIEF DESCRIPTION OF THE DRAWINGS

FIG. 7A is a cross-sectional view of another embodiment of an oxygen sensor assembly that is included in an anesthesia machine, wherein an embodiment of a control valve is shown in an open state;

DETAILED DESCRIPTION

Figure 1:
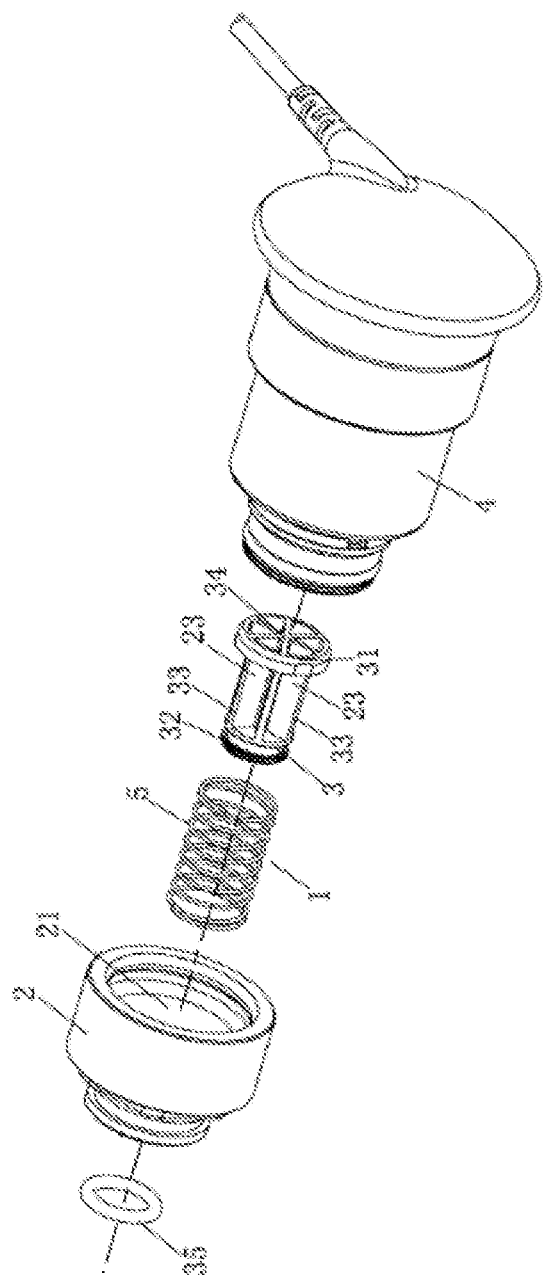
FIG. 1 is an isometric exploded view of an embodiment of an oxygen sensor assembly.
Figure 2:
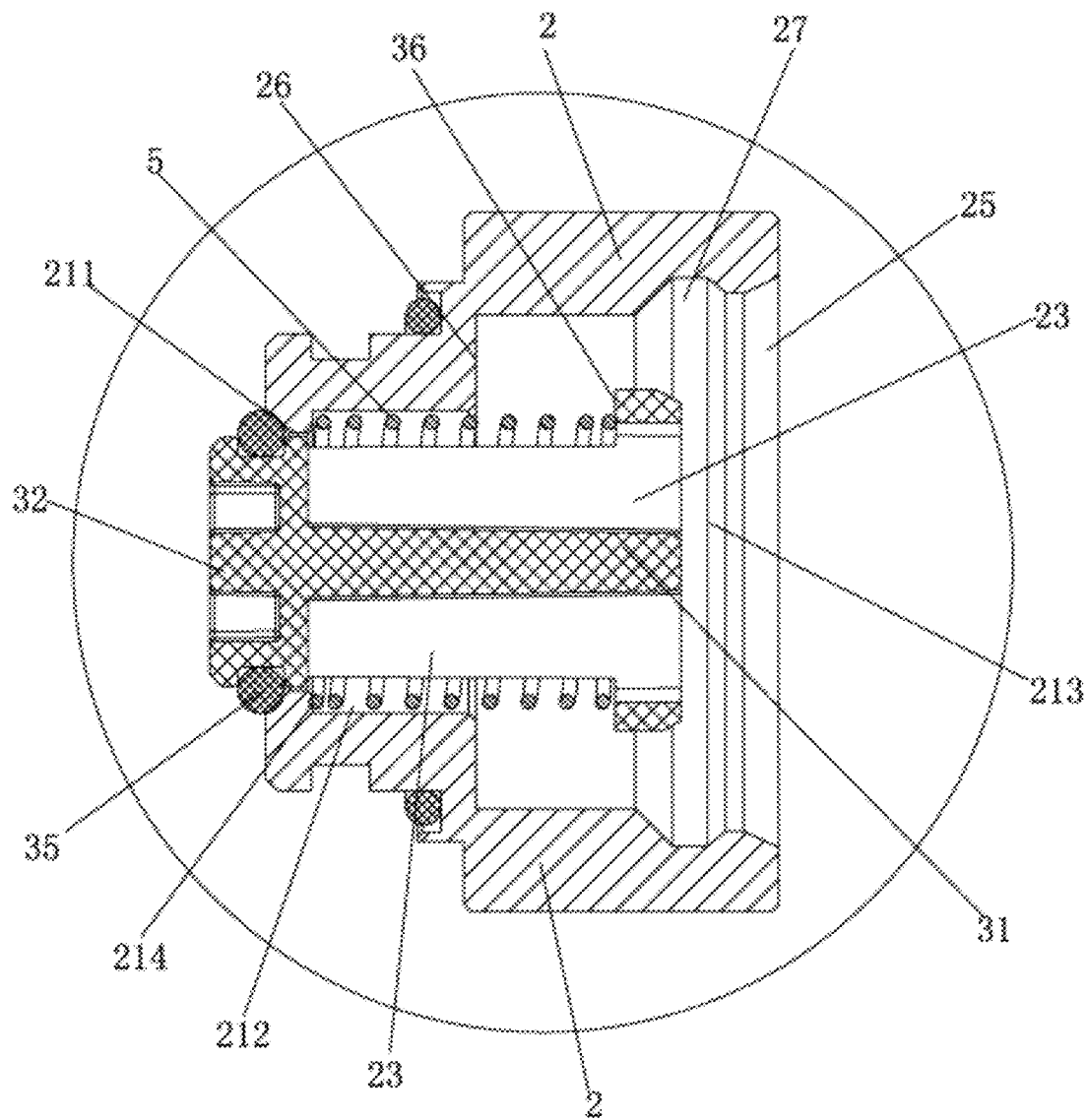
FIG. 2 is a cross-sectional view of an oxygen sensor seat assembly portion of the oxygen sensor assembly of FIG. 1.

Oxygen sensors can be used to detect the oxygen concentration of a fresh gas in an anesthesia machine. An oxygen sensor can be installed in an installation hole of a breathing system gas path of the anesthesia machine. In general, the oxygen sensor is calibrated on at least a daily basis. During calibration, the oxygen sensor is placed in the ambient air, which has an oxygen concentration of 21%. During such calibration, the installation hole is desirably sealed so as to avoid gas leakage from the breathing system gas path and so as to ensure normal ventilation of the breathing system gas path.

Conventionally, there is no end cap at the installation hole. Accordingly, after the oxygen sensor is pulled out, the breathing system gas path is directly communicated with the external ambient air, and no sealing measures are used in the calibration procedure. Therefore, the calibration of the oxygen sensor must generally be completed before the gas is fed into the breathing system gas path, which is inconvenient. If the oxygen sensor is pulled out for calibration after the gas has been fed into the breathing system gas path, the normal ventilation in the breathing system gas path cannot be ensured, and it will cause leakage of anesthetic gases, which contaminates the air and is not environmentally friendly.

In some known systems, an independent end cap is used. The end cap is disposed at the installation hole, and it is plugged into the installation hole after the oxygen sensor is pulled out, so as to ensure normal ventilation in the breathing system gas path. However, this operation is complex and the end cap needs to be properly kept to prevent loss. Stated otherwise, the end cap must be manually inserted into the installation hole during calibration and manually removed from the installation hole after calibration. This can be inconvenient, can require a user to use more than one hand during the calibration procedure, and/or can otherwise complicate and/or lengthen the calibration procedure. Moreover, the end cap can be prone to being lost or contaminated.

The present disclosure is directed to an oxygen sensor seat assembly, an oxygen sensor assembly, and an anesthesia machine, which are capable of preventing gas leakage from the breathing system gas path during calibration of the oxygen sensor unit and provide convenient operation.

In some embodiments, an oxygen sensor seat assembly is provided, which is used for connecting a breathing system gas path of an anesthesia machine and an oxygen sensor unit and includes an oxygen sensor seat and a control valve. The oxygen sensor seat may include a through gas flow passage, which can have a valve port for gases in the breathing system gas path to flow into the gas flow passage. When the oxygen sensor unit is decoupled from the oxygen sensor seat (e.g., is extracted from or otherwise removed or pulled away from the oxygen sensor seat), such as for purposes of calibration of the sensor in the ambient air, the control valve may transition to a closed state (e.g., reset) automatically so as to close the valve port. When the oxygen sensor unit is coupled to or re-coupled with the oxygen sensor seat (e.g., is inserted into the oxygen sensor seat and/or otherwise sealed thereto), such as for purposes of monitoring an oxygen concentration within the gas path of the anesthesia machine, the oxygen sensor unit may automatically cause the control valve to transition to an open state (e.g., drive at least a portion of the control valve to depart from the valve port) to thereby permit the flow of gas to the oxygen sensor unit, thereby permitting the oxygen sensor unit to measure the oxygen concentration of the gas that is in the gas path.

In some embodiments, the control valve may have freedom of linear movement relative to the oxygen sensor seat and may be configured to transition between a closed position and an open position along a substantially linear movement track, path, or pathway. When the oxygen sensor unit is coupled with (e.g., inserted into) the gas flow passage, the oxygen sensor unit may drive a valve body portion of the control valve to move from the closed position to the open position, so that the breathing system gas path, the gas flow passage, and the oxygen sensor unit are in communication with each other. When the oxygen sensor unit is decoupled from (e.g., is removed from) the gas flow passage, the control valve may reset to the closed position automatically and close the valve port.

In some embodiments, the oxygen sensor seat assembly may include an elastic reset member (e.g., a spring) for making a valve body to be reset from the open position to the closed position automatically. The reset member may be disposed between the oxygen sensor seat and the control valve.

In some embodiments, the control valve includes a valve body and a seal portion fixedly connected to each other. The valve body may be used for receiving the driving force of the oxygen sensor unit, and when the control valve is reset to the closed position automatically, the seal portion may seal the valve port.

The seal portion may also include an elastic seal ring. When the control valve is located at the closed position, the seal portion may seal and plug the valve port through the seal ring.

In some configurations, the gas flow passage includes at least one diversion channel for guiding the gas flow. The diversion channel may be formed by a fluid guide body. When the control valve is located at the open position, the diversion channel may communicate with the breathing system gas path and the oxygen sensor unit.

The guide body may include at least two guide plates. The valve body may include a central shaft, and the guide plates may be distributed on the central shaft in a radial manner around the central shaft, and a diversion channel may be at least partially defined by two adjacent guide plates.

In some embodiments, the valve body extends inward toward the gas flow passage, and the seal portion extends outward from the gas flow passage. The reset member may be a spring, which is located inside the gas flow passage and is coupled with (e.g., sleeved onto) the valve body. The gas flow passage may have a first stopping step disposed therein, the valve body may include a second stopping step disposed correspondingly therein, and two ends of the spring are pressed against the first stopping step and the second stopping step, respectively.

In some configurations, the valve body and the wall of the gas flow passage form a sliding pair.

An oxygen sensor assembly may be provided, which includes an oxygen sensor unit and the oxygen sensor seat assembly. The oxygen sensor unit may be detachably connected to the gas flow passage of the oxygen sensor seat assembly.

The oxygen sensor unit may be plug-fitted or screw-thread fitted to the gas flow passage.

An anesthesia machine may also provided, which includes a breathing system gas path and the oxygen sensor seat assembly. In some embodiments, the assembly has an auto-close function. That is, after the oxygen sensor unit is pulled outwardly from the anesthesia machine, the control valve can transition automatically to close the valve port, so as to prevent gas leakage from the breathing system gas path. When the oxygen sensor unit is inserted, the oxygen sensor unit can cause (e.g., urge or drive) the control valve to depart from the valve port. In some embodiments, the control valve can guide a gas flow to enter the oxygen sensor, so as to complete the measurement of the oxygen concentration. The structure can close the valve port automatically at any time when the oxygen sensor unit is pulled out, so as to prevent gas leakage. Moreover, operation of the system is convenient, and the risk of gas leakage due to the absence of the end cap is reduced or eliminated.

As shown in FIG. 1 to FIG. 4, an oxygen sensor seat assembly 1 may be installed in a breathing system gas path of an anesthesia machine and used for connecting the breathing system gas path and an oxygen sensor unit 4. The oxygen sensor seat assembly 1 may include an oxygen sensor seat 2 and a control valve 3. The oxygen sensor seat 2 may include a through gas flow passage 21, which may also be referred to merely as a gas flow passage. The gas flow passage 21 may include a valve port 22, and the gas in the breathing system gas path can flow into the gas flow passage 21 through the valve port 22. The control valve 3 may include a valve body 31 and a seal portion 32 fixedly connected to each other, and the seal portion 32 may be fitted to the valve port 22 of the gas flow passage.

The control valve 3 may be configured to have freedom of linearly moving relative to the oxygen sensor seat 2. Stated otherwise, the control valve 3 can be configured to move freely relative to the oxygen sensor seat 2 in at least a linear direction, or stated in yet another manner, the control valve 3 can be configured to freely translate relative to the oxygen sensor seat 2. The control valve 3 may have a closed position and an open position on a movement track, path, or pathway. Stated otherwise, the control valve 3 may move freely in a linear direction. The control valve 3 may be restrained so as to move linearly along a track, path, or pathway. At a first position along the pathway, the valve can be in a closed position, whereas at a second position along the pathway, the valve can be in an open position. When the control valve 3 is located at the closed position, the seal portion 32 closes the valve port 22 of the oxygen sensor seat 2 to block the gas flow passage 21, so that the gas in the breathing system gas path cannot flow into the oxygen sensor unit 4. When the control valve 3 is located at the open position, the seal portion 32 leaves the valve port 22 to unblock the gas flow passage 21, so that the gas in the breathing system gas path can flow into the oxygen sensor unit 4. When the control valve 3 is located at the open position, the control valve 3 is driven by a reset force that enables the control valve 3 to automatically reset to the closed position.

In a normal state, the control valve 3 is located at the closed position. When the oxygen sensor unit 4 is installed into the gas flow passage 21 of the oxygen sensor seat 2, the oxygen sensor unit 4 presses against the valve body 31 of the control valve 3 and drives the entire control valve 3 to linearly move to the open position. In this process, a driving force of the oxygen sensor unit 4 overcomes the reset force, and the seal portion 32 of the control valve 3 leaves the valve port 22 of the gas flow passage, so that the gas in the breathing system gas path can flow into the oxygen sensor unit 4 through the gas flow passage 21 to facilitate measurement of the oxygen concentration.

When the oxygen sensor unit 4 needs to be calibrated in the air, the oxygen sensor unit 4 is taken out of the gas flow passage 21, and under the effect of the reset force, the control valve 3 resets to the closed position automatically, and the seal portion 32 of the control valve 3 closes the valve port 22 to block the gas flow passage 21, so that the gas in the breathing system gas path cannot flow into the gas flow passage 21. This achieves sealing and prevents gas leakage from the breathing system gas path.

In some embodiments, the reset force is provided by an elastic reset member 5, and the reset member 5 is located between the control valve 3 and the oxygen sensor seat 2. When the oxygen sensor unit 4 is taken out of the gas flow passage 21 of the oxygen sensor seat 2, the reset member 5 enables the control valve 3 to be automatically reset from the open position to the closed position. The reset member 5 could be, for example, a compression spring, a tension spring, a gas spring, a spring leaf, or other similar structures. When the entire oxygen sensor seat assembly 1 is vertically installed, the reset force may be the gravity of the control valve 3. That is, when the oxygen sensor unit 4 is taken out of the gas flow passage 21, the control valve 3 can be reset from the open position to the closed position automatically under by the effect of gravity.

In some embodiments, the gas flow passage 21 may include multiple diversion channels 23 for guiding the gas flow. The diversion channel 23 may be formed by a guide body 33, and the guide body 33 may be disposed on the valve body 31 of the control valve 3. When the control valve 3 is located at the open position, the gas in the breathing system gas path can flow into the oxygen sensor unit 4 through the diversion channels 23. In some embodiments, a single diversion channel 23 and multiple guide bodies 33 could be used.

Another embodiment of the oxygen sensor seat assembly 1 may include an oxygen sensor seat 2, a control valve 3, and a reset member 5. The oxygen sensor seat 2 may include a through gas flow passage 21, which may include a first end 24 and a second end 25 opposite to the first end 24. The first end 24 may include a valve port 22, which may have a larger outer diameter and a smaller inner diameter. The second end 25 may be used for installing the oxygen sensor unit 4 therein.

The control valve 3 may include a valve body 31 and a seal portion 32 fixedly connected to each other. The valve body 31 may include a central shaft 34 and multiple guide plates serving as a guide body 33. The guide plates may be distributed around the central shaft 34 in a radial manner, thus forming a diversion channel 23 between two adjacent guide plates. The seal portion 32 may include an elastic seal ring 35 capable of deforming under force. In some embodiments, the reset member 5 is elastic, and may be a spring.

After the oxygen sensor seat assembly is assembled, the seal portion 32 of the control valve may extend outward from the gas flow passage 21 of the oxygen sensor seat. The valve body 31 of the control valve may extend inwards into the gas flow passage 21. The reset member 5 may be located inside the gas flow passage and may be sleeved on the valve body 31. The two ends of the reset member 5 may be pressed against the valve body 31 and the oxygen sensor seat 2, respectively.

At an initial position, under the elastic force of the reset member 5, the seal portion 32 of the control valve may seal and plug the valve port 22 of the gas flow passage through the seal ring 35, so that the breathing system gas path does not communicate with the ambient air. When it is required to perform oxygen concentration measurement, the oxygen sensor unit 4 may be installed in the gas flow passage 21 through the second end 25 of the gas flow passage. During installation, the reset member 5 is compressed, the oxygen sensor unit 4 drives the control valve 3 to linearly move to the open position through the valve body 31 of the control valve, and, at this time, the seal ring 32 departs from the valve port 22, and the gas in the breathing system gas path flows into the oxygen sensor unit 4 through the valve port and the diversion channel. When calibration is to be performed, the oxygen sensor unit 4 is taken out of the gas flow passage 21, and the reset member 5 recovers or returns to it natural or relaxed position, or its resting state, so that the control valve 3 is automatically reset to the closed position and re-plugs the valve port 22.

With respect to the oxygen sensor seat assembly, the gas flow passage 21 of the oxygen sensor seat 2 may be step-shaped and may include a first gas flow passage 211, a second gas flow passage 212, and a third gas flow passage 213 that are communicated in sequence from outside to inside and have a gradually increased inner diameter. The third gas flow passage 213 may be fitted to the oxygen sensor unit 4, a first stopping step 214 is formed at the junction of the first gas flow passage 211 and the second gas flow passage 212, and a limiting step 26 is formed at the junction of the second gas flow passage 212 and the third gas flow passage 213. The valve body 31 of the control valve may include a second stopping step 36, and two ends of the reset member 5 may be pressed against the first stopping step 214 and the second stopping step 36, respectively.

The third gas flow passage 213 may include a positioning slot 27 recessed on the wall thereof. The oxygen sensor unit 4 may include a positioning ring 41 corresponding to the positioning slot 27. When the oxygen sensor unit 4 is installed, the oxygen sensor unit 4 may be located in the third gas flow passage 213 and pressed against the limiting step 26, and the positioning ring 41 may fall into the positioning slot 27.

With respect to the oxygen sensor seat assembly, the control valve 3 and a wall 210 of the gas flow passage 21 may form a sliding pair, so that the control valve 3 can linearly slide along the wall 210.

Figure 3:
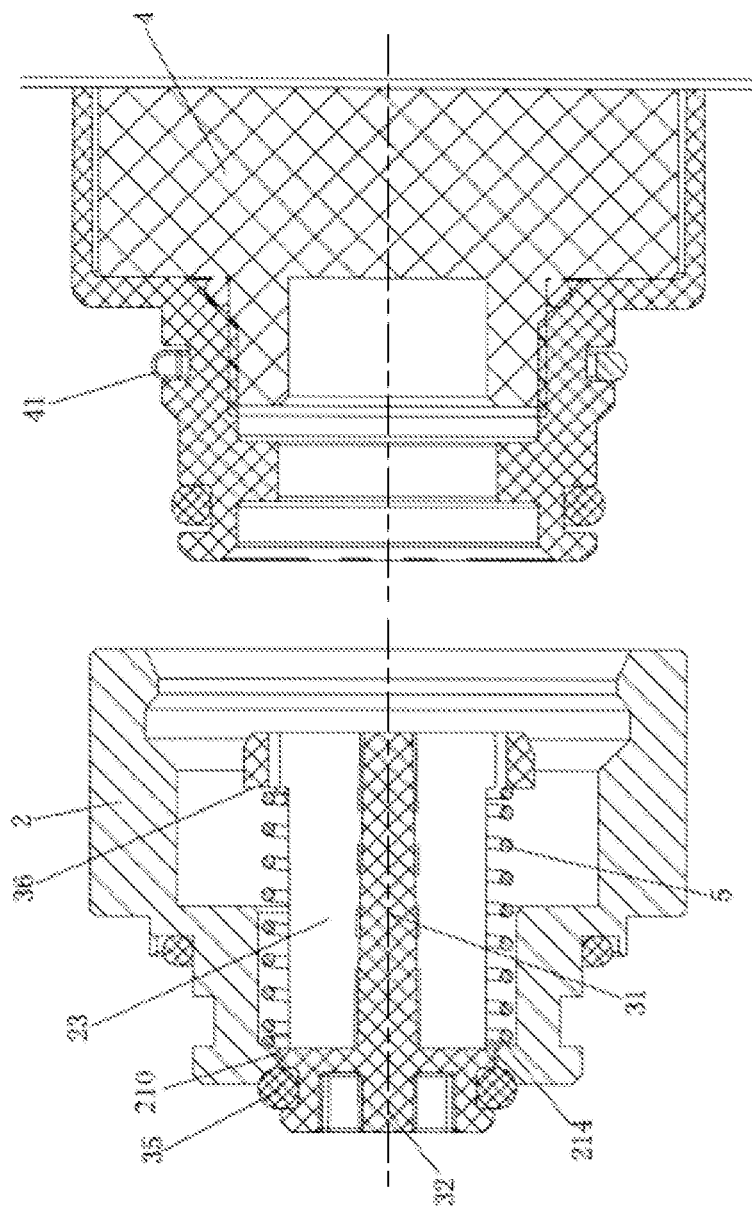
FIG. 3 is a cross-sectional view of the oxygen sensor assembly after an oxygen sensor unit is pulled out.
Figure 4:
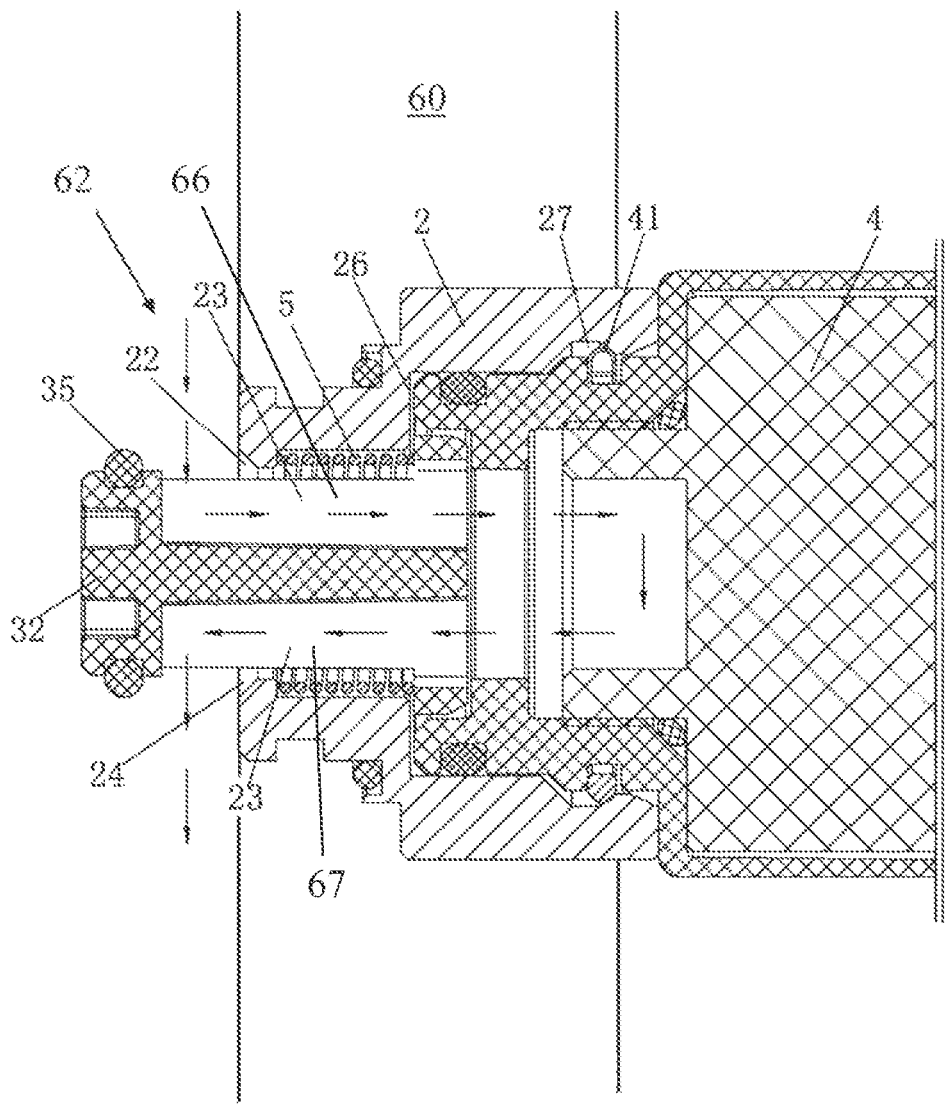
FIG. 4 is a cross-sectional view of the oxygen sensor assembly after the oxygen sensor unit is installed.

With reference to FIGS. 3 and 4, at least a portion of the gas flow passage 21 can be formed by an interior wall or inner surface of a sidewall 50 of the oxygen sensor seat 2. The oxygen sensor unit 4 can include a sealing member 52, such as an O-ring or other suitable sealing device, which can cooperate with the sidewall 50 to form an airtight seal when the oxygen sensor unit 4 is inserted into the oxygen sensor seat 2. Accordingly, when the control valve 3 is in the open position, as shown in FIG. 4, the oxygen sensor unit 4 can cooperate with a portion of the oxygen sensor seat 2 to prevent gases from escaping from an anesthesia machine 60. In particular, the oxygen sensor unit 4 can cooperate with the oxygen sensor seat 2 to prevent gases from escaping from a gas path 62 that is defined by the anesthesia machine 60. The gas path 62 can also be referred to herein as a breathing system gas path or as a gas delivery path, passageway, conduit, or channel. The gas path 62 can be defined by any suitable device capable of conducting gases, such as by tubing or conduit, or by a channel or bore through a plastic or other solid material.

With continued reference to FIG. 4, in some embodiments, the oxygen sensor unit 4 is coupled to the oxygen sensor seat 2, and the gas in the breathing system gas path 62 can flow along the path indicated by the arrows. For example, the gas in the breathing system gas path 62 can flow through the output section 66, the oxygen sensor unit 4 and the input section 67 in sequence, which could facilitate measurement of the oxygen concentration.

Figure 5:
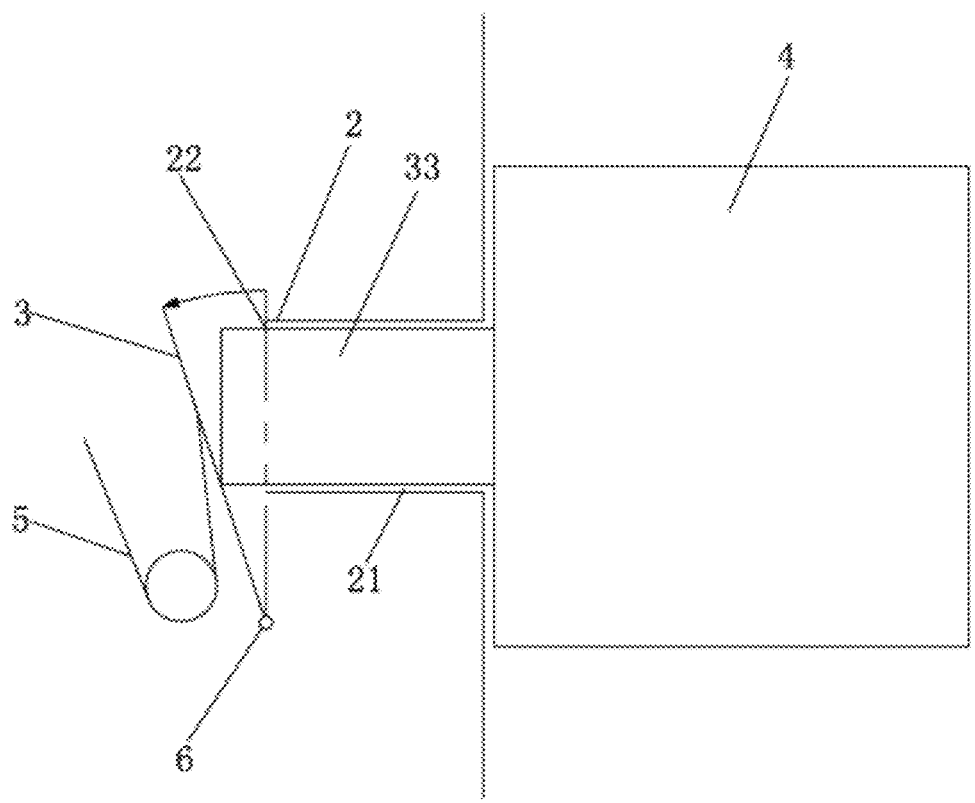
FIG. 5 is a cross-sectional view of an embodiment of an oxygen sensor unit installed into another embodiment of an oxygen sensor assembly.

With reference to FIG. 5, in some embodiments, an oxygen sensor seat assembly may include an oxygen sensor seat 2 and a control valve 3. The oxygen sensor seat 2 may include a through gas flow passage 21, and the gas flow passage 21 may include a valve port 22. The control valve 3 may be rotatably installed at the valve port 22 through a hinge 6, so that the control valve 3 forms a hinge-type valve structure. The control valve 3 may include a closed position and an open position, the reset force for resetting the control valve 3 from the open position to the closed position is provided by a reset member 5, and the reset member 5 is, for example, a torsion spring. The reset member can be compressed between the oxygen sensor seat 2 and the control valve 3.

When the oxygen sensor unit 4 is inserted into the gas flow passage 21, the front end of the oxygen sensor unit 4 pushes the control valve 3 open, so that the control valve 3 rotates to the open position, and the gas in the breathing system gas path can enter the oxygen sensor unit 4. When the oxygen sensor unit 4 is taken out, under the effect of the torsion spring, the control valve 3 rotates to the closed position and closes the valve port 22.

The oxygen sensor unit 4 may include a guide body 33 for guiding the gas flow and may be located at the front end thereof. When the oxygen sensor unit 4 is inserted, the guide body 33 drives the control valve 3 to rotate. The guide body 33 can be configured to translate within the through gas flow passage 21 along a longitudinal path or track. Stated otherwise, the gas flow passage 21 can define a longitudinal path having a longitudinal axis. The control valve 3 can rotate about an axis that is neither collinear with nor parallel to the longitudinal axis, or stated otherwise, the rotational axis can be non-collinear with and nonparallel to the longitudinal axis. For example, in the illustrated embodiment, the control valve 3 is configured to rotate about a rotational axis that extends vertically into and out of the page (i.e., is perpendicular to the plane of the page), whereas the longitudinal path extends from left to right within the plane of the page. Accordingly, in the illustrated embodiment, the control valve 3 rotates about an axis that is perpendicular to a longitudinal axis along which the oxygen sensor unit 4 travels during insertion into and removal from the through gas flow passage 21.

Figure 6:
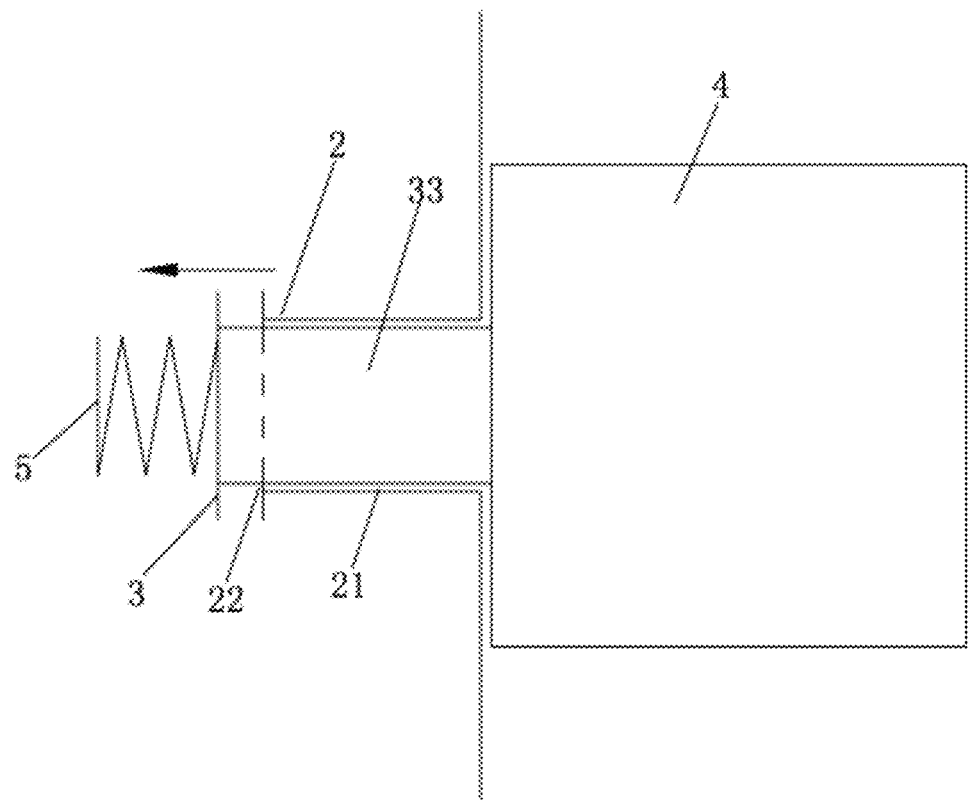
FIG. 6 is a cross-sectional view of an embodiment of an oxygen sensor unit installed into another embodiment of an oxygen sensor assembly.

As shown in FIG. 6, in some embodiments, an oxygen sensor seat assembly may include an oxygen sensor seat 2 and a control valve 3. The oxygen sensor seat 2 may include a through gas flow passage 21, and the through gas flow passage 21 may include a valve port 22. The control valve 3 may be fitted to an end surface of the valve port 22. That is, the control valve 3 is equivalent to a plate-type valve structure. The control valve 3 may have a closed position and an open position.

In some embodiments, the reset force for resetting the control valve 3 from the open position to the closed position is provided by a reset member 5, and the reset member 5 is, for example, a compression spring. The reset member 5 may be connected to the oxygen sensor seat 2 and the control valve 3 and is compressed between the oxygen sensor seat 2 and the control valve 3. However, unlike the embodiment depicted in FIGS. 1-4, the reset member 5 is not positioned within the gas flow passage 21. Rather, the reset member 5 is at an exterior of the gas flow passage 21. When the oxygen sensor unit 4 is inserted, the guide body 33 at a front end of the oxygen sensor unit 4 may push the control valve 3 open, so that the gas flow can enter the oxygen sensor unit 4. When the oxygen sensor unit 4 is taken out, under the effect of the elastic force of the compression spring, the control valve 3 may reset to the closed position and close the valve port 22.

Accordingly, in various embodiments, an oxygen sensor seat assembly may include an oxygen sensor seat and a control valve. The oxygen sensor seat may be used for providing a support or installation position for other elements of the assembly, and the oxygen sensor seat may be an independent element, or may be directly processed on a breathing system gas path of an anesthesia machine. The oxygen sensor seat may include a through gas flow passage. The control valve may include a valve body and a seal portion fixedly connected to each other. The valve body may be used for receiving the driving force of the oxygen sensor unit, and the seal portion may be used for opening or sealing the valve port of the gas flow passage. The seal portion may be an elastic seal ring, such as a standard seal ring having good sealing performance and interchangeability, or may be a seal pad. In some embodiments, the seal portion may be a surface of the control valve.

The gas flow passage may include one or more diversion channels for guiding the gas flow. A diversion channel may be formed by a fluid guide body. When the control valve is located at the open position, the gas in the breathing system gas path can flow into the oxygen sensor unit through the diversion channel. The guide body may be disposed at the control valve, and the guide body may be located inside the gas flow passage. The guide body may also be disposed at the oxygen sensor seat. The guide body may also be disposed at the oxygen sensor unit, and when the oxygen sensor unit is installed into the gas flow passage, the guide body may extend into the gas flow passage and drive the control valve. The guide body may be the guide plate distributed in a radial manner, a diversion pipe, or other structures that can achieve the diversion effect.

The oxygen sensor seat assembly may include a reset member for resetting the control valve. The reset member may be located inside or outside the gas flow passage.

In some embodiments, an oxygen sensor assembly is provided, which includes an oxygen sensor unit and the oxygen sensor seat assembly described above. In further embodiments, the oxygen sensor unit may be detachably installed in the gas flow passage of the oxygen sensor seat assembly. The detachable manner may be, for example, via a plug fitting interface, fastening fitting interface, snap-fitting interface, friction-fitting interface, or threaded interface.

An anesthesia machine may also be provided, which includes a breathing system gas path and the oxygen sensor seat assembly described above.

Figure 7B:
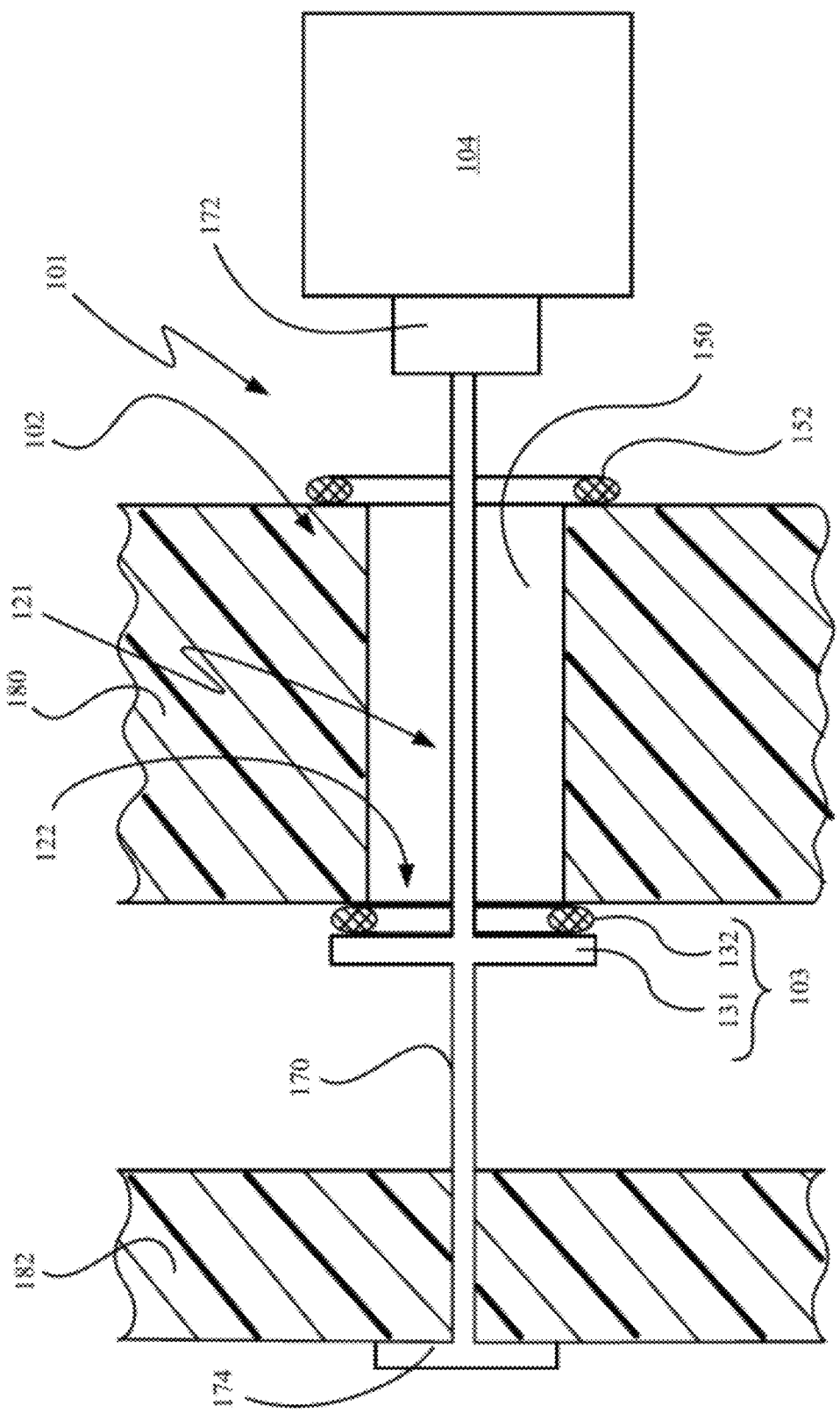
FIG. 7B is another cross-sectional view of the oxygen sensor assembly of FIG. 7A, wherein the control valve is shown in a closed state.
Figure 8A:
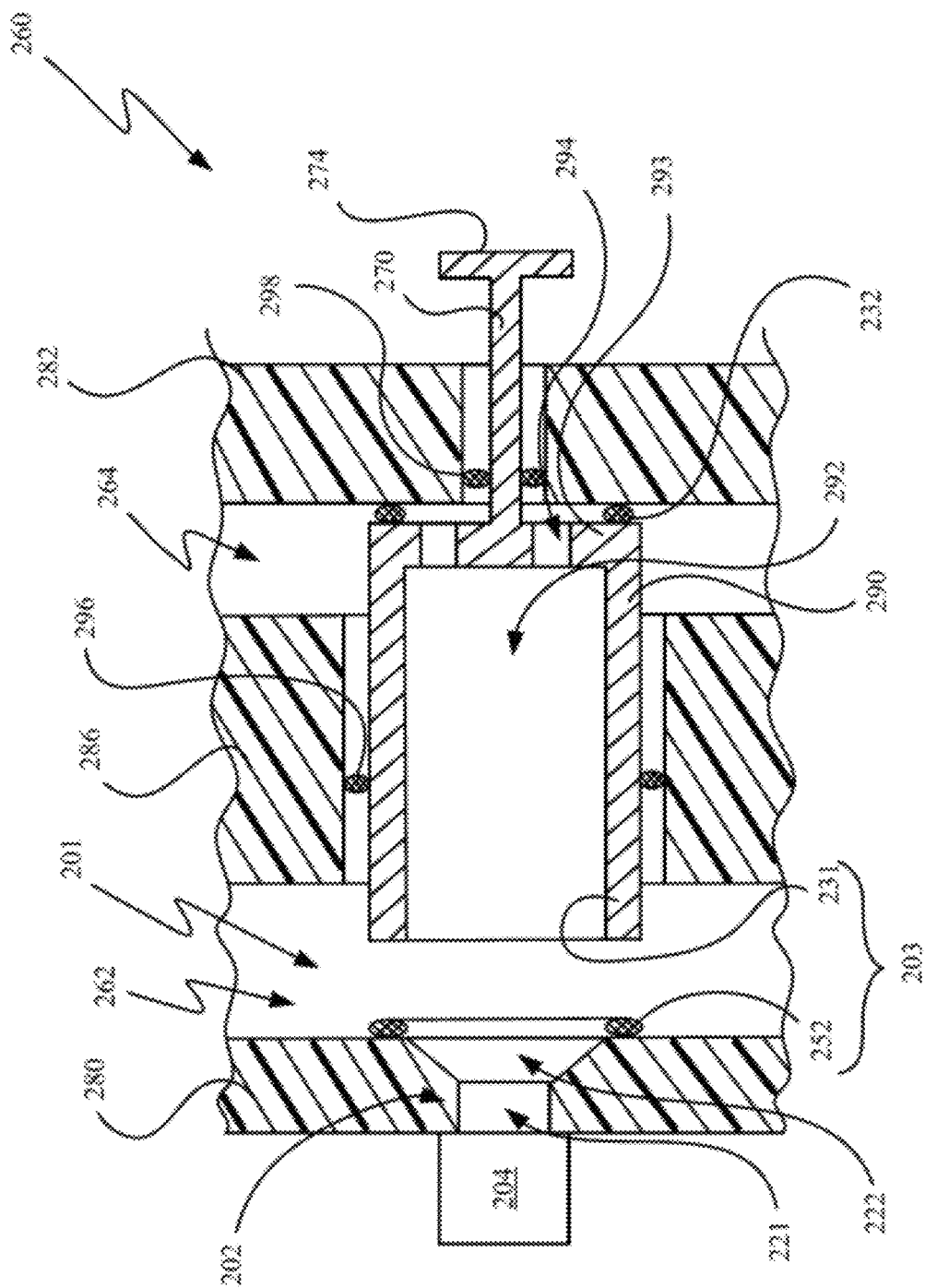
FIG. 8A is a cross-sectional view of another embodiment of an oxygen sensor assembly that is included in an anesthesia machine, wherein another embodiment of a control valve is shown in an open state.
Figure 8B:
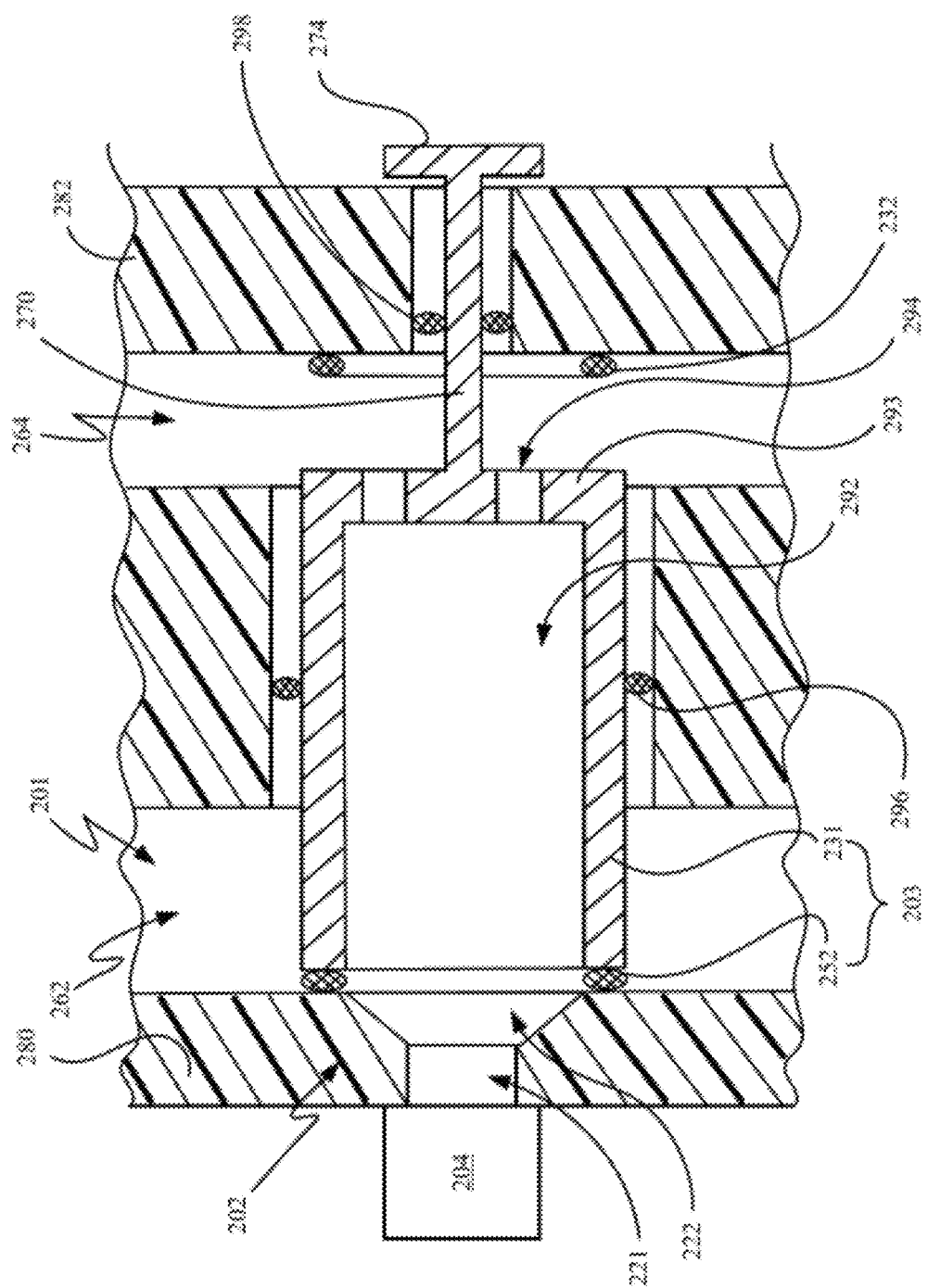
FIG. 8B is another cross-sectional view of the oxygen sensor assembly of FIG. 8A, wherein the control valve is shown in a closed state.

In the embodiments depicted in FIGS. 1-6, the oxygen sensor unit 4 can be completely removed from the anesthesia machine, such as for calibration, or for replacement in the event of malfunction or failure. In other embodiments, as discussed further below, the oxygen sensor unit 4 may remain coupled with the anesthesia machine when it is removed from the gas flow passage 21. An illustrative embodiment of such an assembly is depicted in FIGS. 7A-7B, and is discussed below. In either scenario, the oxygen sensor unit 4 may move relative to the anesthesia machine. In still other embodiments, the oxygen sensor unit 4 may be fixedly coupled to the anesthesia machine, and the control valve 3 can be configured to permit selective communication of either the gas flow passage 21 or a fresh air passage (e.g., calibration passage) with the oxygen sensor unit 4. An illustrative embodiment of such an assembly is depicted in FIGS. 8A-8B, and is discussed below.

FIGS. 7A and 7B illustrate another embodiment of an oxygen sensor seat assembly 101, which may also be referred to herein as an oxygen sensor assembly, an oxygen sensing system, or an oxygen sensing assembly. The oxygen sensor assembly 101 can resemble the previously discussed oxygen sensor assemblies (e.g., the assembly 1 depicted in FIGS. 1-4) in certain respects. Accordingly, like features are designated with like reference numerals, with the leading digits incremented to have a "1" in the hundreds position. Relevant disclosure set forth above regarding similarly identified features thus may not be repeated hereafter. Moreover, specific features of the oxygen sensor assembly 101 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the assembly 101. Any suitable combination of the features and variations of the same described above with respect to the previously discussed oxygen sensor assemblies (e.g., the assembly 1) can be employed with the assembly 101, and vice versa. This pattern of disclosure applies equally to further embodiments depicted in subsequent figures and described hereafter.

With continued reference to FIGS. 7A and 7B, the assembly 101 can be included in an anesthesia machine 160. The assembly 101 may include an oxygen sensor seat 102, a control valve 103, and an oxygen sensor unit 104. In the illustrated embodiment, the oxygen sensor seat 102 is integrally formed with a sidewall 180 or other housing component of the anesthesia machine 160. In other embodiments, the oxygen sensor seat 102 may be formed separately from the sidewall or other housing component and may be joined therewith. For example, the oxygen sensor seat 102 can include a separate piece, such as that shown in FIG. 1. The oxygen sensor seat 102 may define a gas flow passage 121 and a valve port 122. In some embodiments, at least a portion of the gas flow passage 121 is defined by a sidewall 150 of the oxygen sensor seat 102. In some embodiments, a sealing member 152 can be included at a proximal end of the gas flow passage 121.

The control valve 103 may include a valve body 131 and a seal portion 132. In the illustrated embodiment, the valve body 131 includes a disk-shaped protrusion that extends radially outwardly from a shaft 170. The shaft 170 may include a connector 172 at a first or proximal end thereof and may include a stop 174 at a second or distal end thereof. The connector 172 and/or the stop 174 also may each extend radially outwardly from the shaft 170. The connector 172 can be of any suitable variety, and can be configured to selectively or permanently attach the oxygen sensor unit 104 to the shaft 170. The stop 174 may be disk-shaped or define any other suitable shape, and can be configured to prevent the shaft 170 from being pulled through an opening in another sidewall 182 (or other component) of the anesthesia machine 160. The seal portion 132 can be of any suitable variety, such as a gasket (e.g., an O-ring).

With reference to FIG. 7A, the control valve 103 is shown in an open position, configuration, or state. As can be appreciated by comparing FIG. 7B to FIG. 7A, as the oxygen sensor unit 104 is pushed inwardly toward the sidewall 180, the shaft 170 and the valve body 131 move in tandem therewith. This movement separates the valve body 131 from the seal 132, thereby opening the valve port 122. Accordingly, coupling of the oxygen sensor unit 104 with the oxygen sensor seat 102 automatically opens the control valve 103.

A distal surface of the oxygen sensor unit 104 can form a seal with the sealing member 152. The sidewall 150 of the oxygen sensor seat 102 may be configured to frictionally engage the connector 172 so as to retain the oxygen sensor unit 104 in selective, temporary (e.g., non-permanent), secure engagement with the oxygen sensor seat 102. Other suitable arrangements are also possible for engaging the oxygen sensor unit 104 with the oxygen sensor seat 102. For example, rather than a friction-fit engagement between the connector 172 and the sidewall 150, the sidewall 150 can instead form a snap-fit and/or friction-fit engagement with a distal end of the oxygen sensor unit 104, such as described above with respect to FIGS. 1-4. In further embodiments, the sealing member 152 may be positioned about the connector 172 and/or about the oxygen sensor unit 104, rather than at an outer surface of the sidewall 180, and may be received into the gas flow passage 121 so as to form an airtight seal with the sidewall 150.

With the control valve 103 in the open configuration, gas that is within a breathing system gas path 162 can be permitted to enter the valve port 122 and pass through the gas flow passage 121 so as to be analyzed by the oxygen sensor unit 104. Stated otherwise, when the control valve 103 is open, the breathing system gas path 162, the gas flow passage 121, and the oxygen sensor unit 104 can be in fluid communication with each other. The gas flow can resemble that shown in FIG. 4. Although not shown in FIG. 7A, in some embodiments, at least a portion of the shaft 170 can include a guide body, such as described above, which may include radially outwardly projecting guide plates that can form one or more diversion channels that can divert gas flow from the gas flow passage 121 into and/or through the valve port 122.

With reference to FIG. 7B, decoupling of the oxygen sensor unit 104 from the oxygen sensor seat 102 can automatically close the control valve 103. In particular, a connection between the oxygen sensor unit 104 and the connector 172 can cause the shaft 170 to move in tandem with the oxygen sensor unit 104, which can bring the valve body 131 into sealing engagement with the sealing member 132. In some embodiments, a temporary fastener or other temporary engaging system can be used to maintain the oxygen sensor unit 104 in this extended or calibrating orientation, while maintaining the control valve 103 in a sealed or closed state. For example, in some embodiments, the stop 174 may be configured to frictionally or otherwise engage the sidewall 182 so as to maintain the system 101 in the orientation shown in FIG. 7B.

The stop 174 can prevent the shaft 170 from being pulled out of the anesthesia machine 160. Moreover, a distal end of the shaft 170 may remain snugly engaged with the sidewall 182, which can support, stabilize, or counterbalance the oxygen sensor unit 104 at an opposite end of the shaft 170. The arrangement shown can permit the oxygen sensor unit 104 to remain coupled with the anesthesia machine 160 during calibration thereof. Such an arrangement may be convenient for a user, as the oxygen sensor unit 104 may not need to be held during calibration. Moreover, such an arrangement can prevent the oxygen sensor unit 104 from being dropped, damaged, or lost.

FIGS. 8A and 8B illustrate another embodiment of an oxygen sensor assembly 201 that can resemble the previously discussed oxygen sensor assemblies 1, 101 in certain respects. Accordingly, like features are designated with like reference numerals, with the leading digits incremented to have a "2" in the hundreds position. The assembly 201 can be included in an anesthesia machine 260. The assembly 201 may include an oxygen sensor seat 202, a control valve 203, and an oxygen sensor unit 204. In the illustrated embodiment, the oxygen sensor seat 202 is integrally formed with a sidewall 280 or other housing component of the anesthesia machine 260. In other embodiments, the oxygen sensor seat 202 may be formed separately from the sidewall 280 or other housing component and may be joined therewith. The oxygen sensor seat 202 may define a gas flow passage 221 and a valve port 222.

The control valve 203 may include a valve body 231 and one or more seal portions, seal members, or sealing rings 232, 252. In the illustrated embodiment, the valve body 231 includes a cup 290 that is substantially cylindrical and defines a cavity 292. The cup 290 includes an end wall 293 that defines a plurality of apertures, openings, or ports 294 that extend completely through the end wall 293. The valve body 231 can be positioned at a first end of a shaft 270, which may include a stop or handle 274 at a second end thereof. The handle 274 may extend radially outwardly from the shaft 270. In the illustrated embodiment, the handle 274 is substantially disk-shaped, although other suitable arrangements are possible. For example, in some embodiments, the handle 274 can include gripping features that can facilitate grasping thereof for movement of the shaft and valve body 231. For example, the gripping features may include a longitudinally extending protrusion that can be readily be grasped between fingertips of a user. The handle 274 can be configured to prevent the shaft 270 from being pushed through an opening in a sidewall 282 or other component of the anesthesia machine 260. The sealing members 232, 252 can be of any suitable variety, such as a gasket (e.g., an O-ring).

The oxygen sensor unit 204 can be fixedly attached to the oxygen sensor seat 202. For example, in some embodiments, the oxygen sensor unit 204 is permanently attached to the sidewall 280, although in other embodiments, the oxygen sensor unit 204 may be removable from the sidewall 280 (e.g., to permit replacement in case of damage or failure). Stated otherwise, the oxygen sensor unit 204 does not move relative to the oxygen sensor seat 202 during delivery of an anesthetic or during calibration. Instead, the control valve 203 is used to deliver gas from the desired gas source to the oxygen sensor unit 204 without moving the oxygen sensor unit 204, as discussed further below.

The anesthesia machine 260 can include two gas paths 262, 264. The gas path 262 can be similar to the gas paths 62, 162 discussed above, and thus may also be referred to as a breathing system gas path. Gases that flow through the breathing system gas path 262 can include, for example, anesthetic gases mixed with air. The additional gas path 264 can also be referred to as a fresh air environment or as a fresh air channel. In certain of the embodiments discussed above, the oxygen sensor units are removed or displaced from their respective anesthesia machines so as to be introduced into an ambient air environment that is external to the anesthesia machines. In this manner, the oxygen sensor units can be calibrated. However, in the instant embodiment, the oxygen sensor unit 204 is fixedly attached to the anesthesia machine 260, and thus is not removed or displaced from the machine 260 into an ambient air environment for purposes of calibration. Rather, ambient air is diverted from the fresh air channel 264 into communication with the oxygen sensor unit 240. As further discussed below, in some embodiments, the ambient air may be pressurized within the fresh air channel 264.

In the illustrated embodiment, at least a portion of each of the breathing system gas path 262 and the fresh air channel 264 are formed by in inner sidewall 286 of the anesthesia machine 260. Other arrangements are also contemplated. For example, as previously discussed, gas paths can be formed by components other than housing members, such as by tubing or conduit. To maintain an airtight system while permitting movement of the shaft 270 and the valve body 231, sealing members 296, 298 can be provided within the sidewalls 282, 286, as shown in FIGS. 8A and 8B.

With reference to FIG. 8A, the control valve 203 is shown in an open position, configuration, or state. As can be appreciated by comparing FIG. 8B to FIG. 8A, the control valve 203 can be moved into this position by pulling outwardly on the handle 274. This movement separates the valve body 231 from the seal 252, thereby opening the valve port 222 to the gases that are within the breathing system gas path 262. The gases can be permitted to enter the valve port 222 and pass through the gas flow passage 221 so as to be analyzed by the oxygen sensor unit 204. Stated otherwise, when the control valve 203 is open, the breathing system gas path 262, the gas flow passage 221, and the oxygen sensor unit 204 can be in fluid communication with each other.

When the control valve 203 is in the open position, a proximal end thereof forms an airtight seal with the sealing member 232. This prevents air from the fresh air channel 264 from passing through the ports 294. Moreover, the sealing member 296 prevents air from the fresh air channel 264 from migrating into the breathing system gas path 262.

With reference to FIG. 8B, the control valve 203 can be closed by pushing on the handle 274 so as cause a distal end of the valve body 231 to press against the seal member 252 and form an airtight seal therewith. Accordingly, the closed control valve 203 can prevent gas from the breathing system gas path 262 from proceeding to the valve port 222. In the illustrated embodiment, the valve body 231 and the seal 252 member encompass or encircle the valve port 222, and thus prevent access thereto from an exterior of the cup 290 portion of the valve body 231. This seal also prevents gas from exiting from an interior of the cup 290 into the breathing system gas path 262. Moreover, when the control valve 203 is in this closed position, the proximal end thereof is spaced from the sealing member 232, which allows fresh air to pass from the fresh air channel 264 through the ports 294, through the valve port 222, through the gas flow passage 221, and to the oxygen sensor unit 204. Accordingly, when the control valve 203 is in the closed position, or stated otherwise, is in a calibration position, the fresh air channel 264, the valve port 222, the gas flow passage 221, and the oxygen sensor unit 204 are in fluid communication with each other. Accordingly, the oxygen sensor unit 204 can be calibrated when the valve body 231 is in this position.

As previously noted, in some embodiments, it can be desirable for the fresh air that is located within the fresh air channel 264 to be pressurized. This can ensure that anesthetic and other gases are flushed from the chamber 292 and the gas flow passage 221 to allow for accurate calibration of the oxygen sensor unit 204. Relatively high pressures can be used to speed up the flushing procedure, if desired.

In other embodiments, the positions of the fresh air channel 264 and the breathing system gas path 262 can be reversed, such that the fresh air channel 264 is closer to the oxygen sensor unit 204. In such embodiments, the valve body 231 can be in the "closed" position discussed above during an anesthetic procedure and can be moved to the "open" position discussed above to calibrate the oxygen sensor unit 204.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Recitation in the claims of the term "first" with respect to a feature or element does not necessarily imply the existence of a second or additional such feature or element. Embodiments of the invention in which an exclusive property or privilege is claimed are defined as follows.

What is claimed is:

1. An oxygen sensor seat assembly for connecting a breathing system gas path of an anesthesia machine and an oxygen sensor unit, the assembly comprising:
    an oxygen sensor seat comprising a gas flow passage, wherein the gas flow passage comprises a valve port that is configured to permit gas in the breathing system gas path to flow into the gas flow passage, wherein the gas flow passage comprises an input section and an output section; and
    a control valve that is configured to transition between an open position in which the valve port is open and a closed position in which the control valve closes the valve port,
    wherein the control valve is configured to automatically transition to the open position and gas in said breathing system gas path flow through said output section, said oxygen sensor unit and said input section in sequence when the oxygen sensor unit is coupled to the oxygen sensor seat, and wherein the control valve is configured to automatically transition to the closed position when the oxygen sensor unit is decoupled from the oxygen sensor seat.

2. The oxygen sensor seat assembly of claim 1,
    wherein the control valve is configured to freely translate relative to the oxygen sensor seat along a movement pathway;
    wherein the closed position and the open position of the control valve are located along the movement pathway; and
    wherein the oxygen sensor unit is inserted into the gas flow passage when the oxygen sensor unit is coupled with the oxygen sensor seat, wherein, when the oxygen sensor unit is coupled with the oxygen sensor seat, the oxygen sensor unit moves the control valve from the closed position to the open position so that the breathing system gas path, the gas flow passage, and the oxygen sensor unit are in communication with each other, and wherein, when the oxygen sensor unit is removed from the gas flow passage, the control valve automatically resets to the closed position and closes the valve port.

3. The oxygen sensor seat assembly of claim 1, wherein the control valve comprises a valve body, and wherein the oxygen sensor seat assembly further comprises an elastic reset member coupled with the valve body so as to enable the valve body to be automatically reset from the open position to the closed position.

4. The oxygen sensor of claim 3, wherein the elastic reset member is disposed between the oxygen sensor seat and the control valve.

5. The oxygen sensor seat assembly of claim 3, further comprising a seal portion fixedly connected to the valve body, wherein the valve body is configured to receive a driving force from the oxygen sensor unit so as to separate the seal portion from the valve port to thereby open the valve port when the oxygen sensor unit is coupled with the valve port seat, and wherein, when the control valve is automatically reset to the closed position, the seal portion seals the valve port.

6. The oxygen sensor seat assembly of claim 5, wherein the seal portion comprises an elastic seal ring, and wherein, when the control valve is located at the closed position, the seal portion seals the valve port via the seal ring.

7. The oxygen sensor seat assembly of claim 3, wherein a portion of the valve body is at an interior of the gas flow passage and the seal portion is at an exterior of the gas flow passage when the control valve is in the open position, wherein the reset member comprises a spring that is located inside the gas flow passage and is coupled to the valve body, wherein the gas flow passage has a first stopping step disposed therein, wherein the valve body has a second stopping step correspondingly disposed therein, and wherein two ends of the spring are pressed against the first stopping step and the second stopping step, respectively.

8. The oxygen sensor seat assembly of claim 3, wherein the valve body and the wall of the gas flow passage are a sliding pair.

9. The oxygen sensor seat assembly of claim 1, wherein the gas flow passage comprises multiple diversion channels for guiding gas flow, wherein at least a portion of the diversion channels is formed by a fluid guide body, and wherein, when the control valve is in the open position, the breathing system gas path and the oxygen sensor unit are in communication with each other via the diversion channels.

10. The oxygen sensor seat assembly of claim 9, wherein the guide body comprises two or more guide plates, wherein the valve body comprises a central shaft, wherein the guide plates are distributed on the central shaft in a radial manner around the central shaft, and wherein a diversion channel is formed between two adjacent guide plates.

11. The oxygen sensor seat assembly of claim 1, wherein the gas flow passage comprises one diversion channel, wherein at least a portion of the diversion channel is divided into multiple channels by multiple guide bodies, and wherein, when the control valve is in the open position, the breathing system gas path and the oxygen sensor unit are in communication with each other via the multiple channels.

12. An oxygen sensor assembly configured to permit selective communication between an oxygen sensor unit and one of a breathing system gas path of an anesthesia machine and a fresh air environment, the assembly comprising:
    an oxygen sensor unit;
    an oxygen sensor seat configured to be coupled with an anesthesia machine, wherein the oxygen sensor seat comprises a gas flow passage and a valve port, wherein the gas flow passage comprises an input section and an output section; and
    a control valve configured to selectively open and close the valve port, wherein movement of the control valve to a first position places the oxygen sensor unit in fluid communication with a breathing system gas path of an anesthesia machine via the gas flow passage of the oxygen sensor seat, and wherein the control valve is configured to be in a second position when the oxygen sensor unit is in fluid communication with a fresh air environment;
    wherein when said oxygen sensor unit is in fluid communication with said breathing system gas path, gas in said breathing system gas path flows through said output section, said oxygen sensor unit and said input section in sequence.

13. The oxygen sensor assembly of claim 12, wherein the oxygen sensor unit is separate from the control valve and is configured to selectively interact therewith.

14. The oxygen sensor assembly of claim 13, wherein the oxygen sensor is configured to be selectively inserted into and removed from the oxygen sensor seat, wherein insertion of the oxygen sensor unit into the oxygen sensor seat automatically moves the control valve to the first position so as to open the valve port, and wherein removal of the oxygen sensor unit from the oxygen sensor seat causes the control valve to automatically move to the second position so as to close the valve port.

15. The oxygen sensor assembly of claim 14, further comprising an elastic member that is configured to automatically transition the control valve from the first position to the second position.

16. The oxygen sensor seat assembly of claim 12, wherein the gas flow passage comprises multiple diversion channels for guiding gas flow, wherein at least a portion of the diversion channels is formed by a fluid guide body, and wherein, when the control valve is in the first position, the breathing system gas path and the oxygen sensor unit are in communication with each other via the diversion channels.

17. The oxygen sensor seat assembly of claim 12, wherein the gas flow passage comprises one diversion channel, wherein at least a portion of the diversion channel is divided into multiple channels by multiple guide bodies, and wherein, when the control valve is in the second position, the breathing system gas path and the oxygen sensor unit are in communication with each other via the multiple channels.

18. An anesthesia machine comprising:
- a breathing system gas path, wherein the gas flow passage comprises an input section and an output section;
- an oxygen sensor unit;
- an oxygen sensor seat comprising a valve port; and
- a control valve that is configured to transition between a first position and a second position, wherein, when the control valve is in the first position, the control valve permits gas in said breathing system gas path to flow through said output section, said oxygen sensor unit and said input section in sequence, and wherein when the control valve is in the second position, the control valve prevents gas from flowing through the valve port from the breathing system gas path.

19. The anesthesia machine of claim 18, wherein the oxygen sensor unit is separate from the control valve and is configured to selectively interact therewith.

20. The anesthesia machine of claim 19, wherein the oxygen sensor unit is configured to be selectively inserted into and removed from the oxygen sensor seat, and wherein insertion of the oxygen sensor unit into the oxygen sensor seat automatically moves the control valve to the first position so as to open the valve port, and removal of the oxygen sensor unit from the oxygen sensor seat causes the control valve to automatically move to the second position so as to close the valve port.

21. The anesthesia machine of claim 20, further comprising an elastic member that is configured to automatically transition the control valve from the first position to the second position.

22. The anesthesia machine of claim 18, wherein the gas flow passage comprises multiple diversion channels for guiding gas flow, wherein at least a portion of the diversion channels is formed by a fluid guide body, and wherein, when the control valve is in the first position, the breathing system gas path and the oxygen sensor unit are in communication with each other via the diversion channels.

23. The anesthesia machine of claim 18, wherein the gas flow passage comprises one diversion channel, wherein at least a portion of the diversion channel is divided into multiple channels by multiple guide bodies, and wherein, when the control valve is in the second position, the breathing system gas path and the oxygen sensor unit are in communication with each other via the multiple channels.

* * * * *